United States Patent [19]

Grosse

[11] Patent Number: 5,665,081
[45] Date of Patent: Sep. 9, 1997

[54] ODOR ABSORBING ANAL PAD

[76] Inventor: Kenneth J. Grosse, 431 Osborne Ave., Morrisville, Pa. 19067

[21] Appl. No.: 494,950

[22] Filed: Jun. 26, 1995

[51] Int. Cl.⁶ .............................. A61F 13/15; A61F 13/20
[52] U.S. Cl. ................................. 604/359; 604/385.1
[58] Field of Search ........................ 604/358, 357, 604/385.1, 328, 355, 386, 387; 600/30, 32; 128/834

[56] References Cited

U.S. PATENT DOCUMENTS

| | | | |
|---|---|---|---|
| 2,066,946 | 1/1937 | Reiman | 604/359 |
| 2,331,355 | 10/1943 | Strongson | 604/385.1 |
| 2,418,907 | 4/1947 | Schreiber | 604/359 |
| 2,690,415 | 9/1954 | Shuler | 604/359 |
| 2,742,042 | 4/1956 | Flanders | 604/359 |
| 3,490,454 | 1/1970 | Goldfarb et al. | 604/349 |
| 3,905,372 | 9/1975 | Denkinger | 604/359 |
| 4,182,335 | 1/1980 | Matrullo | 604/359 |
| 4,657,808 | 4/1987 | Maggs | 604/360 |
| 4,804,380 | 2/1989 | Lassen et al. | 604/385.1 |

FOREIGN PATENT DOCUMENTS 0389023  9/1990  European Pat. Off. ............ 604/359

*Primary Examiner*—Mark O. Polutta

[57] ABSTRACT

A pad for attenuating sound and absorbing odor from an anal region of an individual. The inventive device includes a pad member containing a volume of odor-absorbing granulated charcoal covered by a layer of filler material and encapsulated within a flexible web. A gluteus insert extends from the pad for positioning between the gluteus-maximus muscles and against the anal region of the user to attenuate noise emanating therefrom.

1 Claim, 3 Drawing Sheets

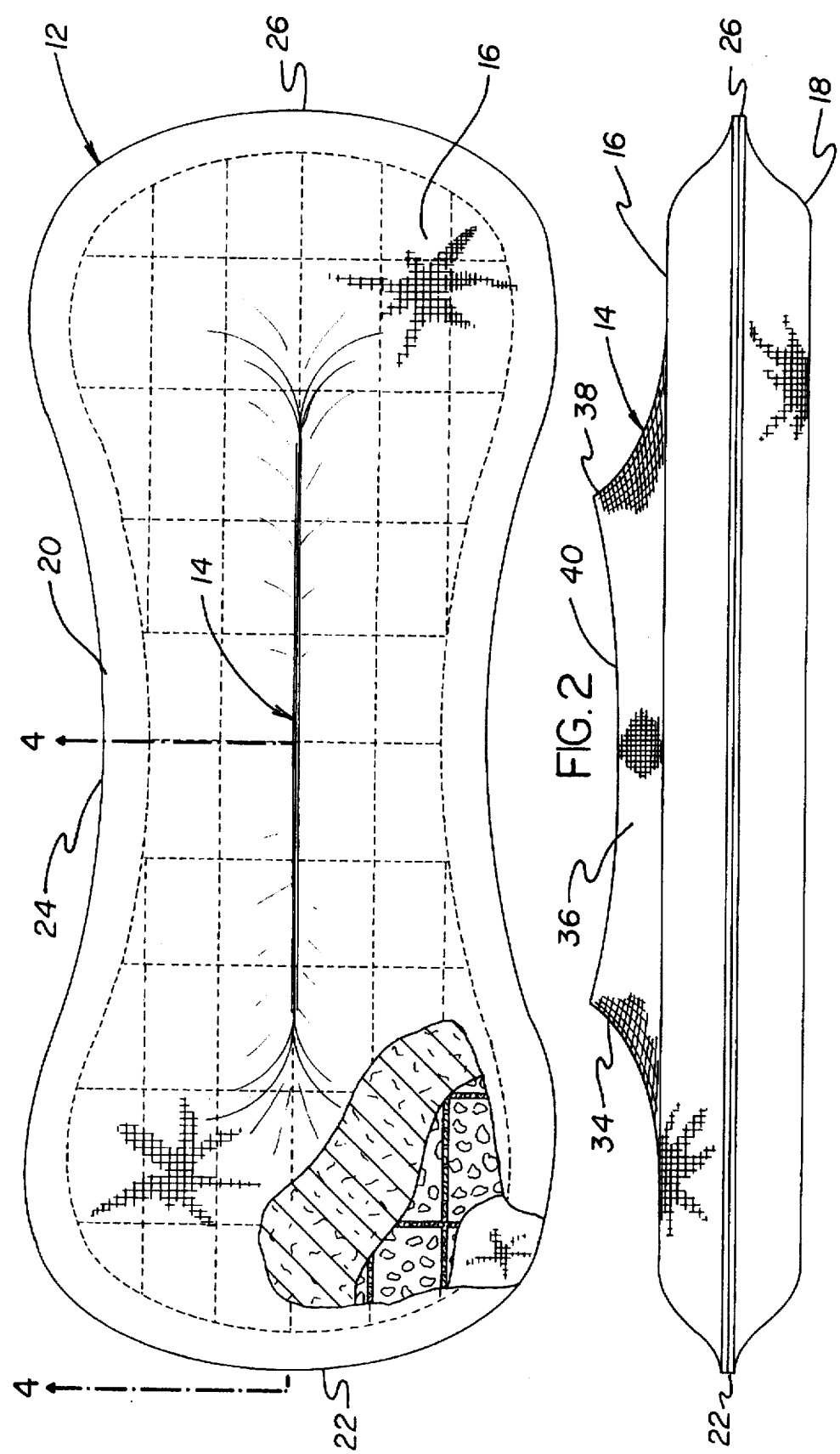

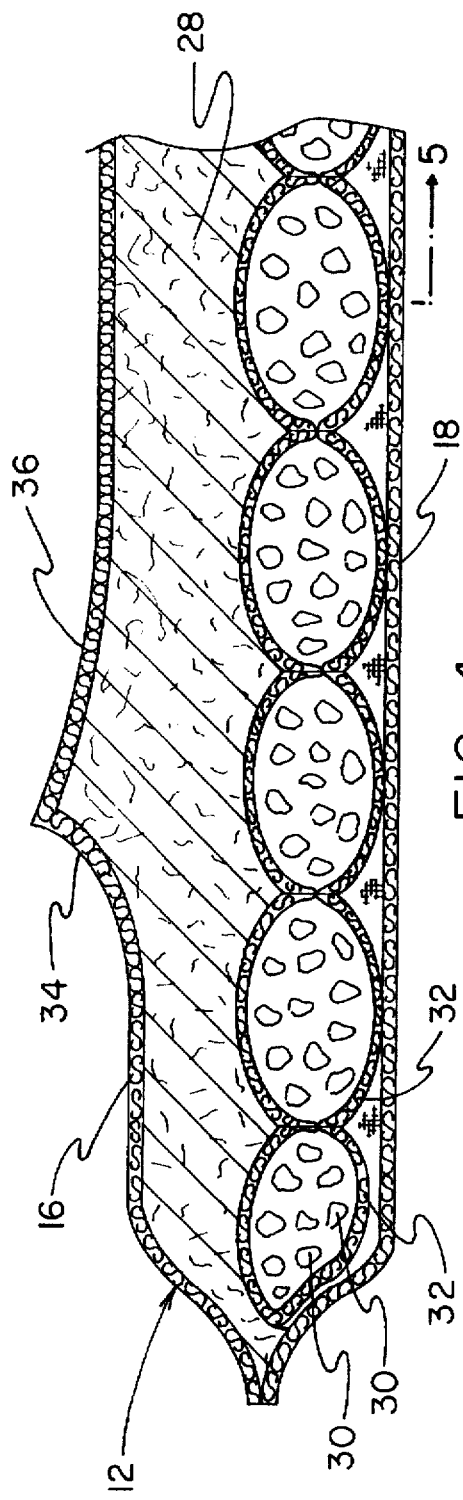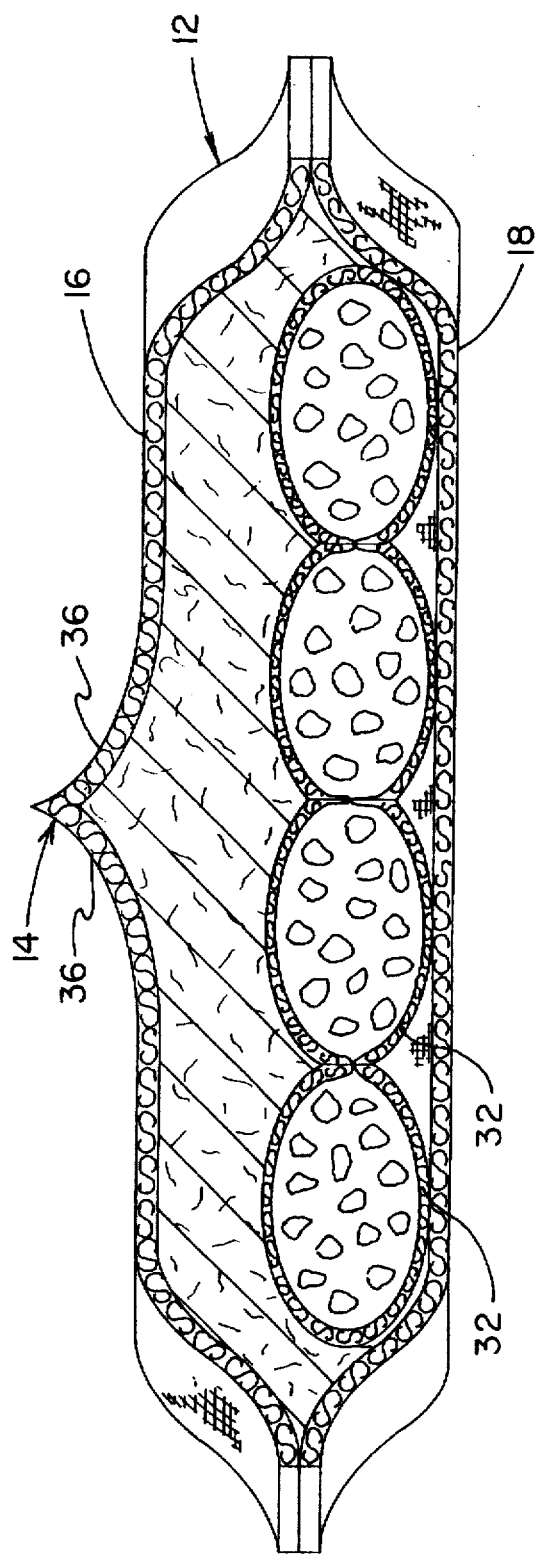

_5,665,081_

ODOR ABSORBING ANAL PAD

BACKGROUND OF THE INVENTION

1. Field of the Invention

The present invention relates to sanitary pads and more particularly pertains to a odor absorbing anal pad for attenuating sound and absorbing odor from an anal region of an individual.

2. Description of the Prior Art

The use of sanitary pads is known in the prior art. More specifically, sanitary pads heretofore devised and utilized are known to consist basically of familiar, expected and obvious structural configurations, notwithstanding the myriad of designs encompassed by the crowded prior art which have been developed for the fulfillment of countless objectives and requirements.

Known prior art sanitary pads include U.S. Pat. No. 5,256,159; U.S. Pat. No. 5,197,208; U.S. Pat. No. 4,663,780; U.S. Pat. No. 5,122,407; U.S. Pat. No. 3,805,785; and U.S. Pat. No. 5,203,806.

While these devices fulfill their respective, particular objectives and requirements, the aforementioned patents do not disclose a odor absorbing anal pad for attenuating sound and absorbing odors from an anal region of an individual which includes a pad member containing a volume of odor-absorbing granulated charcoal covered by a layer of filler material and encapsulated within a flexible web, and a gluteus insert extending from the pad for positioning between the gluteus-maximus muscles and against the anal region of the user to attenuate noise emanating therefrom.

In these respects, the odor absorbing anal pad according to the present invention substantially departs from the conventional concepts and designs of the prior art, and in so doing provides an apparatus primarily developed for the purpose of attenuating sound and absorbing odor from an anal region of an individual

SUMMARY OF THE INVENTION

In view of the foregoing disadvantages inherent in the known types of sanitary pads now present in the prior art, the present invention provides a new odor absorbing anal pad construction wherein the same can be utilized for muffling sound and absorbing odor from a posterior anal region of an individual. As such, the general purpose of the present invention, which will be described subsequently in greater detail, is to provide a new odor absorbing anal pad apparatus and method which has many of the advantages of the sanitary pads mentioned heretofore and many novel features that result in a odor absorbing anal pad which is not anticipated, rendered obvious, suggested, or even implied by any of the prior art sanitary pads, either alone or in any combination thereof.

To attain this, the present invention generally comprises a pad for attenuating sound and absorbing odor from an anal region of an individual. The inventive device includes a pad member containing a volume of odor-absorbing granulated charcoal covered by a layer of filler material and encapsulated within a flexible web. A gluteus insert extends from the pad for positioning between the gluteus-maximus muscles and against the anal region of the user to attenuate noise emanating therefrom.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new odor absorbing anal pad apparatus and method which has many of the advantages of the sanitary pads mentioned heretofore and many novel features that result in a odor absorbing anal pad which is not anticipated, rendered obvious, suggested, or even implied by any of the prior art sanitary pads, either alone or in any combination thereof.

It is another object of the present invention to provide a new odor absorbing anal pad which may be easily and efficiently manufactured and marketed.

It is a further object of the present invention to provide a new odor absorbing anal pad which is of a durable and reliable construction.

An even further object of the present invention is to provide a new odor absorbing anal pad which is susceptible of a low cost of manufacture with regard to both materials and labor, and which accordingly is then susceptible of low prices of sale to the consuming public, thereby making such odor absorbing anal pads economically available to the buying public.

Still yet another object of the present invention is to provide a new odor absorbing anal pad which provides in the apparatuses and methods of the prior art some of the advantages thereof, while simultaneously overcoming some of the disadvantages normally associated therewith.

Still another object of the present invention is to provide a new odor absorbing anal pad for attenuating sound and absorbing odor from an anal region of an individual.

Yet another object of the present invention is to provide a new odor absorbing anal pad which includes a pad member containing a volume of odor-absorbing granulated charcoal covered by a layer of filler material and encapsulated within a flexible web, and a gluteus insert extending from the pad for positioning between the gluteus-maximus muscles and against the anal region of the user to attenuate noise emanating therefrom.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 2 is a top plan view thereof.

FIG. 3 is a side elevation view of the invention.

FIG. 4 is a cross sectional view taken along line 4—4 of FIG. 2.

FIG. 5 is a cross sectional view taken along line 5—5 of FIG. 4.

DESCRIPTION OF THE PREFERRED EMBODIMENT

Figure 1:
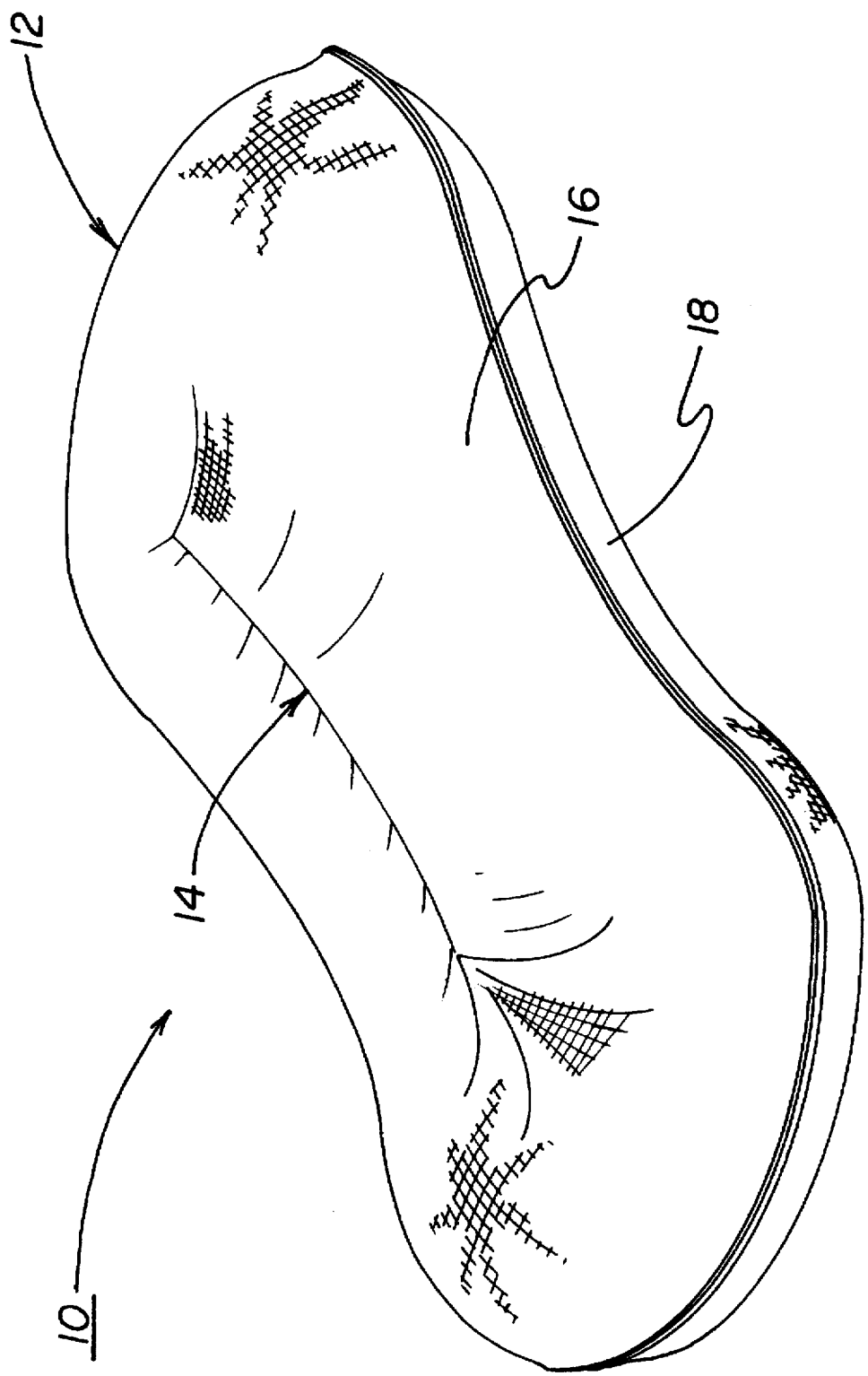
FIG. 1 is an isometric illustration of an odor absorbing anal pad according to the present invention.

With reference now to the drawings, and in particular to FIGS. 1–5 thereof, a new odor absorbing anal pad embodying the principles and concepts of the present invention and generally designated by the reference numeral 10 will be described.

More specifically, it will be noted that the odor absorbing anal pad 10 comprises a pad member 12 positionable into an abutting relationship with an anal region of an individual so as to extend between laterally disposed gluteus-maximus muscles of the individual. A gluteus insert 14 extends from an upper surface of the pad member 12 for wedging positioning between the gluteus-maximus muscles and into direct contact with an anus of the individual. By this structure the gluteus insert 14 closely abuts the anus of the individual so as to attenuate noise emanating therefrom, with the pad member 12 operating to filter gas directed from the individual and absorb odor therefrom.

Referring now to FIGS. 1 through 5 wherein the present invention 10 is illustrated in detail, it can be shown that the pad member 12 of the present invention 10 includes an upper web 16 coupled to a lower web 18. The webs 16 and 18, as shown in FIG. 2, are shaped so as to define an outer peripheral edge 20 of the pad member 12 which extends from a first end 22 of the pad member, along a medial portion 24, and about a second end 26 of the pad member. The pad member 12 is shaped so as to be enlarged at the first and second ends 22 and 26 such that a transverse width of the pad member 12 proximal to the medial portion 24 thereof is substantially less than a transverse width of the pad member 12 proximal either of the first and second ends 22 and 26.

As best illustrated in FIGS. 4 and 5, it can be shown that the pad member 12 further comprises a filler material 28 positioned between the upper web 16 and the lower web 18. Further, a volume of granulated charcoal 30 is positioned in adjacency relative to the filler material 28 and between the upper and lower webs 16 and 18. Preferably, the pad member 12 further comprises a matrix of permeable chambers 32 extending coextensively between the upper web 16 and the lower web 18. Each of the matrix of chambers 32 contains a predetermined volume of the granulated charcoal 30 therewithin. By this structure, gas directed from individual will be forced through the granulated charcoal 30 which operates to filter and absorb odor from such gas.

As best illustrated in FIGS. 3 through 5, it can be shown that the gluteus insert 14 of the present invention 10 projects from an upper surface of the pad member 12 and is preferably formed as an extension of the upper web 16. To this end, the upper web 16, as a result of the filler material 28 positioned therebeneath, is caused to assume a shape of the gluteus insert 14 defining a first end wall 34 of substantially V-shape extending upwardly from the pad member 12 proximal to the first end 22 thereof. Lateral walls 36 extend upwardly from the upper surface of the pad member 12 and parallel to a longitudinal axis directed through the first and second ends 22 and 26 of the pad member. The gluteus insert 14 further includes a second end wall 38 extending upwardly from the upper surface of the pad member 12 proximal to the second end 26 thereof. The second end wall 38 is also substantially V-shaped in configuration, with the lateral walls 36 preferably being substantially concave so as to follow a natural curve of the elongated recess of an anal region of an individual. As best shown in FIG. 3, the gluteus insert 14 includes a medial portion 40 thereof located centrally between the first and second end walls 34 and 38. The gluteus insert 14 preferably extends a first distance from the upper surface of the pad member 12 at the first and second end walls 34 and 38 thereof, and tapers to a second distance from the upper surface of the pad member 12 at the medial portion 40 thereof, wherein the first distance is substantially greater than the second distance so as to define the shape illustrated in FIG. 3 of the drawings. By this structure, the gluteus insert 14 can be closely positioned into a abutting relationship with the anal region of an individual so as to reside between the gluteus-maximus muscles and, therefore, operate to attenuate noise directed from the individual.

In use, the odor absorbing anal pad 10 of the present invention can be easily and comfortably worn by an individual beneath underwear or other selected clothing. The present invention 10 operates to permit an individual to pass anal gas without suffering from the embarrassment of noticeable noise and/or odor.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by LETTERS PATENT of the United States is as follows:

1. An odor absorbing anal pad comprising:

a pad member positionable into an abutting relationship with an anal region of an individual, the pad member comprising an upper web, and a lower web coupled to the upper web, the webs being shaped so as to define an outer peripheral edge of the pad member which extends from a first end of the pad member, along a medial portion thereof, and about a second end of the pad member, the pad member shaped so as to be enlarged at the first and second ends thereof such that a transverse width of the pad member proximal to the medial portion thereof is substantially less than a transverse width of the pad member proximal either of the first and second ends of the pad member, the pad member having a filler material positioned between the upper web and the lower web, a volume of granulated charcoal positioned in adjacency relative to the filler material and between the upper and lower webs, the pad member having a matrix of permeable chambers extending coextensively across an entire length and width and interior of the pad member and being positioned between the upper web and the lower web, each of the matrix of chambers containing a predetermined volume of granulated charcoal therewithin;

a gluteus insert extending from an upper surface of the pad member for wedging positioning between gluteus-maximus muscles and into direct contact with an anus of the individual, the gluteus insert projects from an upper surface of the pad member and is formed as an extension of the upper web, the upper web of the pad member is caused to assume a shape of the gluteus insert defining a first end wall of substantially V-shape extending upwardly from the pad member proximal to the first end thereof, lateral walls extending upwardly from the upper surface of the pad member and parallel to a longitudinal axis directed through the first and second ends of the pad member, and a second end wall of substantially V-shape extending upwardly from the upper surface of the pad member proximal to the second end thereof, the lateral walls are substantially concave in shape so as to follow a natural curve of an elongated recess of an anal region of an individual, the gluteus insert including a medial portion thereof located centrally between the first and second end walls, the gluteus insert extending a first distance from the upper surface of the pad member at the first and second end walls thereof, and tapering to a second distance from the upper surface of the pad member at the medial portion thereof, wherein the first distance is substantially greater than the second distance.

* * * * *